United States Patent
Smith et al.

(10) Patent No.: US 11,793,540 B2
(45) Date of Patent: Oct. 24, 2023

(54) MEDICAL DEVICE WITH A FLOW CONTROLLER

(71) Applicant: Boston Scientific Scimed, Inc., Maple Grove, MN (US)

(72) Inventors: Paul Smith, Smithfield, RI (US); Ryan V. Wales, Northborough, MA (US); Sean P. Fleury, Minneapolis, MN (US); Laura Elizabeth Christakis, Framingham, MA (US); Scott E. Brechbiel, Acton, MA (US); Jeff Gray, Sudbury, MA (US); Mingxiang Xu, Wayland, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 750 days.

(21) Appl. No.: 16/111,372

(22) Filed: Aug. 24, 2018

(65) Prior Publication Data
US 2019/0059925 A1    Feb. 28, 2019

Related U.S. Application Data

(60) Provisional application No. 62/551,398, filed on Aug. 29, 2017.

(51) Int. Cl.
*A61B 17/32* (2006.01)
*A61B 17/3203* (2006.01)
(Continued)

(52) U.S. Cl.
CPC .. *A61B 17/3203* (2013.01); *A61B 17/320016* (2013.01); *A61B 18/14* (2013.01);
(Continued)

(58) Field of Classification Search
CPC ............... A61B 17/3203; A61B 18/14; A61B 17/320016; A61B 2018/00982;
(Continued)

(56) References Cited

U.S. PATENT DOCUMENTS

| | | | | | |
|---|---|---|---|---|---|
| 4,668,215 | A | * | 5/1987 | Allgood | A61M 1/772 604/236 |
| 5,100,377 | A | * | 3/1992 | Freitas | A61M 1/772 604/249 |
| 9,328,485 | B2 | * | 5/2016 | Shaffer | F16K 11/07 |
| 2007/0237977 | A1 | * | 10/2007 | Thomsen | C23C 18/20 205/261 |
| 2010/0217151 | A1 | * | 8/2010 | Gostout | A61B 10/02 600/565 |

(Continued)

FOREIGN PATENT DOCUMENTS

JP    2012239528  A  * 12/2012

OTHER PUBLICATIONS

Orabi, H., Bouhout, S., Morissette, A., Rousseau, A., Chabaud, S., Bolduc, S. (2013). Tissue engineering of urinary bladder and urethra: Advances from bench to patients. The Scientific World Journal, 2013, 1-13. https://doi.org/10.1155/2013/154564 (Year : 2013).*

*Primary Examiner* — Joseph A Stoklosa
*Assistant Examiner* — Annie L Shoulders
(74) *Attorney, Agent, or Firm* — Bookoff McAndrews, PLLC

(57) ABSTRACT

A system for controlling the flow of fluid through a medical device may include a medical device having a lumen that extends to a distal end of the medical device; a fluid source configured to supply fluid having a positive pressure to the lumen of the medical device; and a flow controller configured to apply a negative pressure to the fluid within the lumen, wherein the flow controller is triggered to apply the negative pressure upon a lowering of the positive pressure from the fluid source.

20 Claims, 11 Drawing Sheets

(51) Int. Cl.
*A61B 18/14* (2006.01)
*A61B 18/00* (2006.01)
*A61B 17/00* (2006.01)
*A61B 17/34* (2006.01)
*A61B 17/30* (2006.01)

(52) U.S. Cl.
CPC ..... *A61B 17/32037* (2013.01); *A61B 17/3478* (2013.01); *A61B 18/1492* (2013.01); *A61B 2017/00269* (2013.01); *A61B 2017/306* (2013.01); *A61B 2018/00601* (2013.01); *A61B 2018/00744* (2013.01); *A61B 2018/00982* (2013.01); *A61B 2218/002* (2013.01)

(58) Field of Classification Search
CPC .......... A61B 2218/002; A61B 18/1492; A61B 2018/00744
See application file for complete search history.

(56) References Cited

U.S. PATENT DOCUMENTS

| | | | | |
|---|---|---|---|---|
| 2011/0282382 A1* | 11/2011 | McAlister | ............... | A61M 5/19 606/213 |
| 2012/0179161 A1* | 7/2012 | Rains | ................... | A61B 17/164 606/80 |
| 2015/0045825 A1* | 2/2015 | Caplan | ............. | A61M 25/0084 606/191 |
| 2015/0272665 A1* | 10/2015 | Govari | ............... | A61B 18/1492 604/500 |
| 2015/0297259 A1* | 10/2015 | Matsubara | ............ | A61M 25/04 606/185 |
| 2016/0242844 A1* | 8/2016 | Orczy-Timko | ........ | A61M 39/24 606/80 |
| 2017/0007324 A1* | 1/2017 | Kadamus | ............... | A61B 5/0036 |
| 2017/0112361 A1* | 4/2017 | Surti | .................. | A61B 1/00101 |
| 2020/0237977 A1* | 7/2020 | Panotopoulos | ..... | A61M 1/0058 |

* cited by examiner

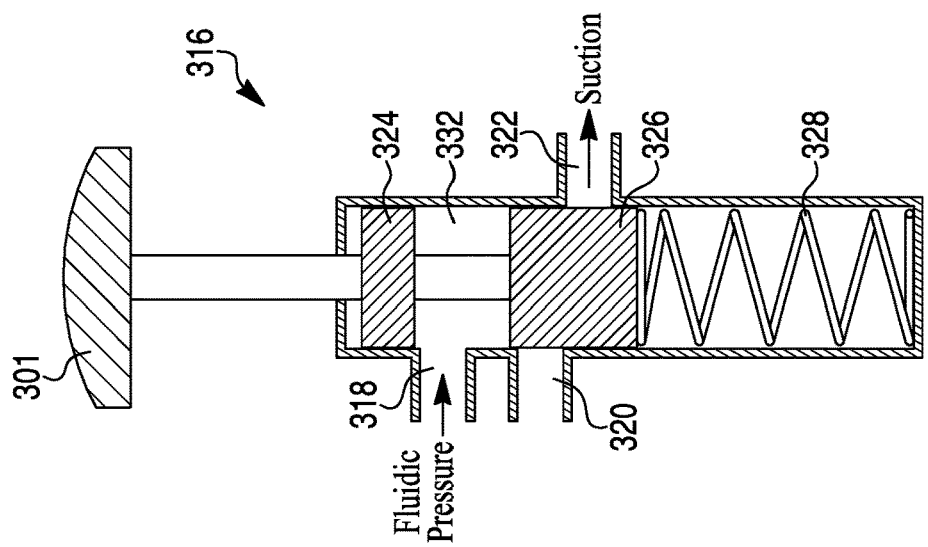
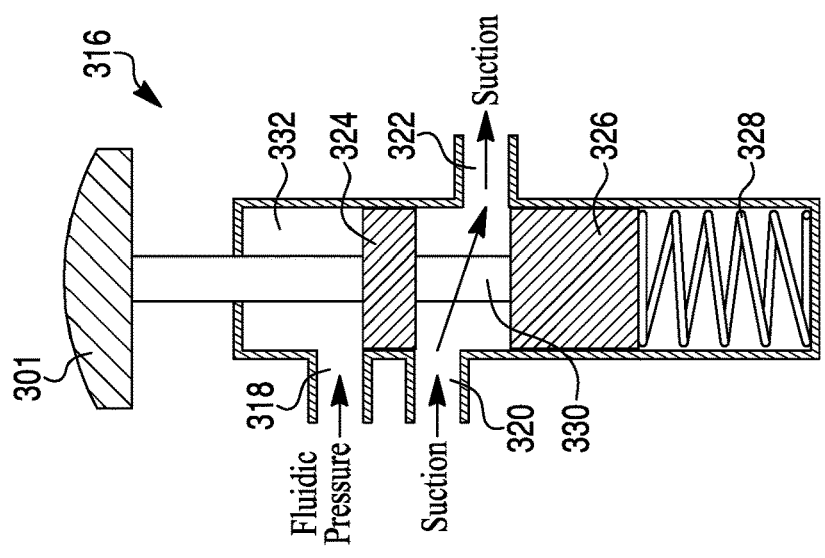
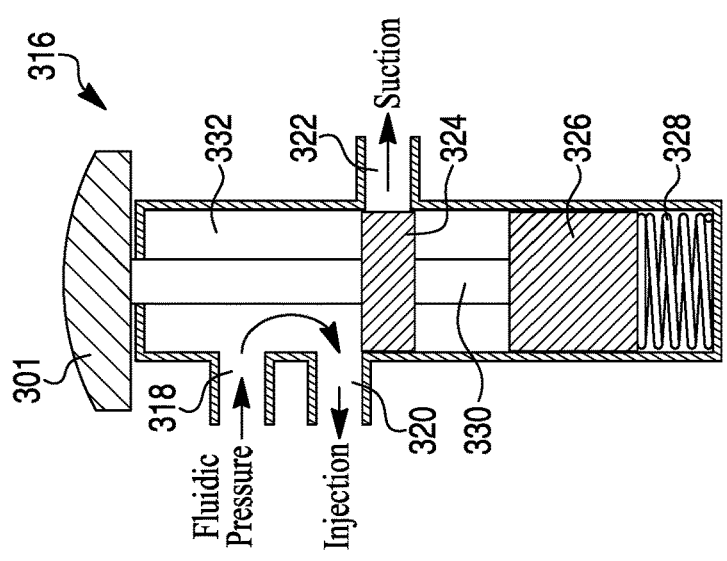

MEDICAL DEVICE WITH A FLOW CONTROLLER

CROSS-REFERENCE TO RELATED APPLICATION

This nonprovisional patent application claims benefit under 35 U.S.C. § 119 to U.S. Provisional Patent Application No. 62/551,398, filed Aug. 29, 2017, the entirety of which is incorporated herein by reference.

TECHNICAL FIELD

The present disclosure relates generally to a medical device with a flow controller. More specifically, the flow controller may apply a negative pressure to alter the flow of fluid through a lumen of the medical device.

BACKGROUND

In various medical procedures, such as endoscopic submucosal dissection (ESD), a medical device may be used to inject a fluid into tissue (e.g., submucosa) of a patient. The fluid may raise a lesion to allow the tissue to be resected. Certain ESD devices may both inject fluid into tissue and resect the tissue using an electrosurgical cutting tool (e.g., knife, needle, or other cutting device). The electrosurgical cutting tool may apply monopolar high-frequency energy to the tissue.

Medical devices used during ESD procedures further may include an elongated catheter or other component having a lumen. During a medical procedure, positive pressure may be applied to fluid within the lumen either manually (e.g., by the user) or by a pump, causing fluid to flow from the distal end of the medical device. When the user (e.g., physician or other health professional) wants to stop the flow of fluid from the distal end, the user may either stop the manual application of pressure, or release a button or otherwise communicate to the pump to stop fluid flow. However, residual pressure within the catheter may continue to eject fluid from the distal end of the medical device, even after the user stops the application of additional positive pressure by turning off the pressure source or otherwise communicating a desire to stop fluid flow. Furthermore, when fluid is retained within the distal end of the medical device, and the distal tip (e.g., of a cutting tool) is subsequently heated, the heat may dry the stagnant fluid, leaving behind salts or other solids that may clog the cutting tool.

SUMMARY

Examples of the present disclosure relate to, among other things, systems, devices, and methods that may apply a negative pressure to stop a fluid flow or alter the flow of fluid through a lumen of a medical device. Each of the examples disclosed herein may include one or more of the features described in connection with any of the other disclosed examples.

In one example, a system for controlling the flow of fluid through a medical device may include a medical device having a lumen that extends to a distal end of the medical device; a fluid source configured to supply fluid having a positive pressure to the lumen of the medical device; and a flow controller configured to apply a negative pressure to the fluid within the lumen, wherein the flow controller is triggered to apply the negative pressure upon a lowering of the positive pressure from the fluid source.

Any of the systems described herein may include one or more of the following features: the medical device may be configured to eject fluid from the distal end of the medical device during the supply of fluid having a positive pressure from the fluid source; and the application of negative pressure by the flow controller may be configured to at least one of: 1) slow or stop a flow of fluid from the distal end of the medical device, or 2) cause fluid to flow in a proximal direction within the lumen; the flow controller may include a valve; the flow controller may include a component movable between a first configuration and a second configuration and biased to the first configuration, wherein a flow of fluid having the positive pressure is configured to cause the component to move from the first configuration to the second configuration, and the lowering of positive pressure is configured to allow the component to move from the second configuration to the first configuration, and movement of the component from the second configuration to the first configuration is configured to cause the negative pressure to be applied to the lumen; the flow controller may include a solenoid; the lowering of the positive pressure may be configured to cause an electrical signal to be sent to the flow controller to cause the flow controller to apply the negative pressure to the fluid within the lumen; the electrical signal may cause at least a portion of the flow controller to move from a first position to a second position to apply the negative pressure; the flow controller may include a power supply; the flow controller may include a container biased to an expanded configuration, the fluid source may include the container, and the medical device may include an electrosurgical cutting tool; the container may include at least one ring to bias the container to the expanded configuration; the flow controller may further include an electromagnet and a magnet configured to compress the container to a collapsed configuration; the flow controller may include a reservoir fluidly connected to the lumen of the medical device, the reservoir being separate from the fluid source, and the reservoir being configured to: supply fluid to the lumen during a flow of fluid from the fluid source, and withdraw fluid from the lumen after removal of a positive pressure source or a signal to the fluid source to discontinue the flow of fluid; the system may further include a pump configured to apply the positive pressure to the fluid from the fluid source; the medical device may include an electrosurgical cutting tool; or the medical device may include a visualization system.

In another example, a method for performing a medical procedure may include introducing a distal end of a medical device to a region proximate a target tissue; applying a positive pressure to a fluid within a lumen of the medical device to cause fluid to exit the distal end; lowering the application of the positive pressure, wherein lowering the application of positive pressure triggers a flow controller to apply negative pressure to the fluid within the lumen; and cutting the target tissue.

Any of the methods disclosed herein may include one or more of the following features or steps: introducing the distal end of the medical device to a region proximate a target tissue may include inserting the distal end into a submucosal layer of tissue; when the flow controller applies the negative pressure, fluid within the lumen may flow in a proximal direction; the medical device may include an electrosurgical cutting tool, and cutting the target tissue may include cutting the target tissue using the electrosurgical cutting tool; the lowering of the application of positive pressure may cause an electrical signal to be sent to the flow controller to cause the flow controller to apply the negative pressure to the fluid within the lumen; the electrical signal may cause at least a portion of the flow controller to move from a first position to a second position; the flow controller may include at least one of a valve, a solenoid, or an electromagnet; the flow controller may include the valve, and the valve may have a first port configured to be fluidly connected to a fluid source, a second port configured to be fluidly connected to the distal end of the medical device, and a third port configured to be fluidly connected to a vacuum source; or the flow controller may include an electromagnet, and during the application of the positive pressure, the electromagnet may be magnetized, and lowering the application of the positive pressure may include lowering the magnetic strength of the electromagnet.

In yet another example, a method for performing a medical procedure may include introducing a distal end of a medical device to a region proximate a target tissue; applying a positive pressure to a fluid within a lumen of the medical device to cause the fluid to exit the distal end of the medical device and enter a space underneath or within the target tissue; and lowering the application of positive pressure, wherein lowering the application of positive pressure triggers a flow controller to apply negative pressure to the fluid within the lumen to stop a flow of fluid from the distal end of the medical device.

Any of the methods disclosed herein may include one or more of the following features or steps: the method may further comprise cutting the target tissue using the medical device; the lowering of the application of positive pressure may cause an electrical signal to be sent to the flow controller to cause the flow controller to apply the negative pressure to the fluid within the lumen; the flow controller may include a valve having a first port configured to be fluidly connected to a fluid source, a second port configured to be fluidly connected to the distal end of the medical device, and a third port configured to be fluidly connected to a vacuum source, and lowering the application of positive pressure may cause the valve to block fluid communication between the first and second ports and open fluid communication between the second and third ports; the flow controller may be a solenoid, and a distal end of the solenoid may be fluidly connected to a fluid circuit between a fluid source and the distal end of the medical device; or lowering the application of positive pressure below a predefined threshold may activate the solenoid.

It may be understood that both the foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal."

BRIEF DESCRIPTION OF THE DRAWINGS

The accompanying drawings, which are incorporated in and constitute a part of this specification, illustrate examples of the present disclosure and together with the description, serve to explain the principles of the disclosure.

FIGS. 3A, 3B, and 3C illustrate a valve flow controller for applying negative pressure to a fluid lumen, according to an exemplary embodiment.

DETAILED DESCRIPTION

The present disclosure is drawn to systems, devices, and methods for controlling fluid flow through a fluid lumen. In particular, the systems, devices, and methods may have or use a flow controller to at least one of slow or stop a fluid flow from a distal end of a medical device, and in some examples, cause fluid to flow from the distal end of the medical device towards a proximal end of the medical device (reverse fluid flow). The fluid lumen may be part of a medical device used for ESD procedures. During the ESD procedure, the medical device may be used to both inject fluid into tissue (e.g., a submucosal layer) and to resect tissue using an electrosurgical cutting tool. The flow controllers described herein, however, can be used with other types of medical devices during any other type of procedure during which controlling fluid flow may be desirable. Although ESD procedures are described herein, reference to ESD procedures should not be construed as limiting the possible applications of the flow controller.

Figure 1:
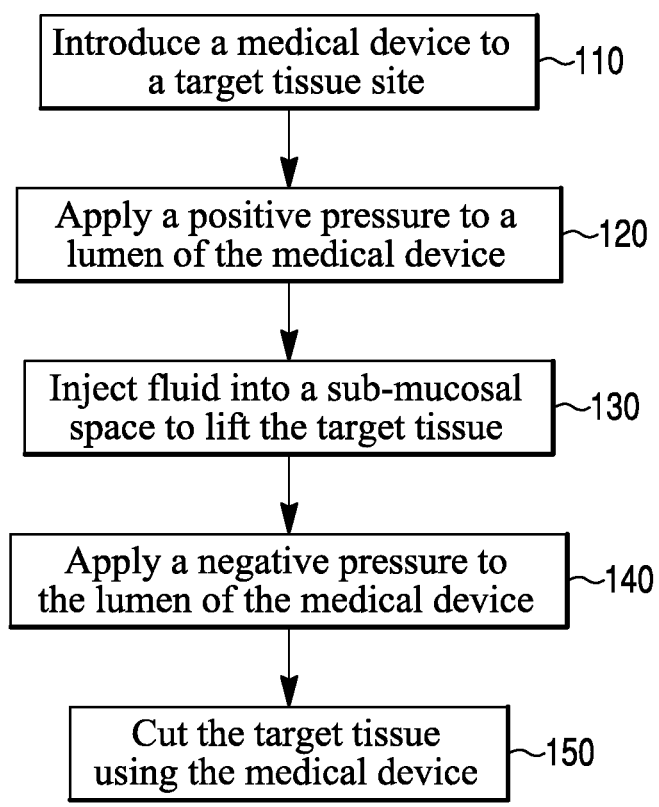
FIG. 1 illustrates a flow chart of a method for performing a medical procedure, according to an exemplary embodiment.

FIG. 1 illustrates an exemplary method for performing a medical procedure. In step 110, a medical device may be introduced to a target tissue site. During this step, a distal end of the medical device may be positioned proximate the target tissue. For example, the distal end may be positioned outside of the patient (e.g., if the target tissue is skin), within a body cavity of the patient (e.g., if the target tissue is a portion of the gastrointestinal tract), or through an opening in the outer layer of target tissue, whether the target tissue is on an exterior of the patient or within a body cavity. The medical device may be any device used to eject fluid during a medical procedure, such as an ESD procedure, and may include devices used to cut tissue (e.g., using fluid or electrical energy), devices used to fill spaces with fluid (e.g., to lift tissue for resection), or devices used to irrigate during a medical procedure. In some examples, when being used to fill spaces with fluid, the medical device may be positioned underneath the target tissue, and when being used to cut tissue, the medical device may be positioned adjacent to the target tissue, either outside of the patient or inside of a body cavity.

In step 120, a positive pressure may be applied to a lumen of the medical device. As used herein, positive pressure means pressure in a direction of a distal end of a medical device, with the distal end of the medical device being the end farthest from the user and/or closest to the patient when the device is being used during a procedure. In contrast, negative pressure, as used herein, means pressure in the opposite direction from positive pressure (e.g., towards the user and/or away from the patient when the device is being used during a medical procedure). In certain examples, positive pressure may cause fluid to flow from a distal end of the medical device (e.g., net positive pressure), and negative pressure may cause fluid to slow or stop its flow towards the distal end of the medical device, and/or to flow towards a proximal end of the medical device (reverse the flow direction) (e.g., net negative pressure). Adjusting an amount of positive pressure may include supplying or terminating a source of positive pressure and/or applying an amount of negative pressure to increase or decrease the net amount of positive pressure. Thus, for example, lowering an application of a positive pressure may include turning off a positive pressure and/or applying a negative pressure. In certain examples, the medical device may include a cutting tool, and positive pressure may cause fluid to flow through a lumen of the cutting tool and out of a distal end of the cutting tool.

Step 130 may include injecting fluid into a space within a body, such as a submucosal space to lift a target tissue. In this example, the distal end of the medical device (e.g., the distal end of a cutting tool) may have been positioned in the submucosal layer of the patient. Positive pressure applied to the lumen may cause fluid to flow from the distal end of the medical device into the submucosal layer.

Once the fluid has been injected a desired amount (e.g., the tissue has been lifted a desired amount), step 140 may include applying a negative pressure to the lumen of the medical device or otherwise lowering an application of positive pressure to the lumen. The negative pressure may slow or stop the flow of fluid from the distal end of the medical device, and/or may reverse the direction of fluid flow and cause fluid to flow towards the proximal end of the medical device.

Optionally, step 150 may include performing a therapeutic operation on the body, for example, cutting the target tissue using the medical device. In some examples, the medical device may include a cutting tool (e.g., knife, needle, etc.) that operates using high-frequency monopolar energy. The negative pressure applied in step 140 may have removed fluid from at least a portion of the lumen of the cutting tool. Accordingly, during step 150, at least a portion of the lumen of the cutting tool may be free of fluid.

Figure 2A:
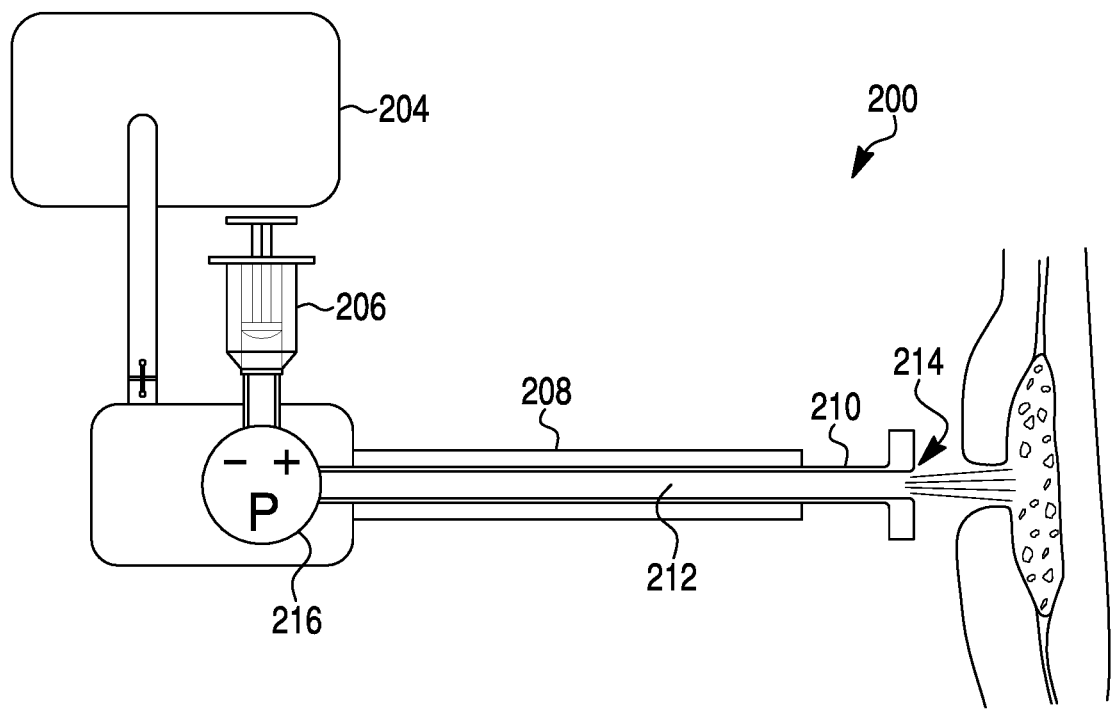
FIGS. 2A and 2B illustrate systems for performing a medical procedure, according to exemplary embodiments.
Figure 2B:
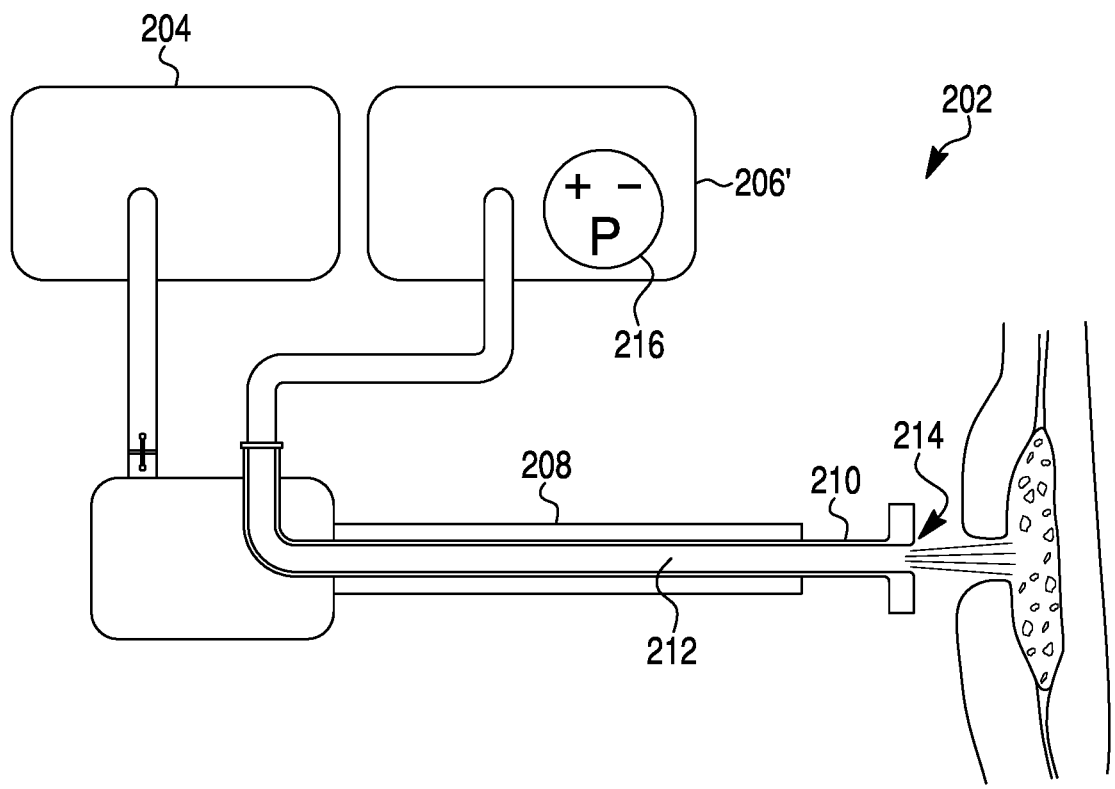

FIGS. 2A and 2B illustrate exemplary systems 200, 202 for performing a medical procedure. Any of the systems and devices described herein may be used to perform the method described in connection with FIG. 1. Both systems 200, 202 may include an energy source 204, a fluid source 206, 206', respectively, a medical device 208 having a cutting tool 210, and a flow regulator 216. Energy source 204 may be a high-frequency energy source electrically connected (e.g., via wires, not shown) to cutting tool 210. The medical device 208 may be any device with any combination of attachments used to perform a medical procedure in which fluid is ejected out of a distal end 214 of the device. For example, medical device 208 may be an endoscope with or without a cutting tool 210 temporarily or permanently fixed to its distal end. Medical device 208 may further include a visualization system (not shown) that includes a light source and a system to transmit image signals from the distal end of the device to the viewer (e.g., optic fibers). Furthermore, medical device 208 may include a lumen 212. Lumen 212 may include a working channel of medical device 208 and/or a lumen extending through cutting tool 210.

A fluid source 206, 206' may at certain times be in fluid communication with lumen 212. System 200 illustrates fluid source 206 as a container, such as a syringe, that may be manually operated by a user to supply pressurized fluid to lumen 212. In other words, operation of fluid source 206 (e.g., by a pressure source) may apply positive pressure to fluid within lumen 212. The pressure source operating on fluid source 206 may be a user (e.g., the hand or foot of a user) or any control mechanism configured to apply pressure to the fluid within fluid source 206. System 202 illustrates an alternative embodiment, in which fluid source 206' is integrated into a pump or other device that can be controlled (e.g., by electronics and/or computer software) to apply a desired amount of pressure to fluid source 206'. The pathway between fluid source 206, 206' (or any other fluid source described herein) and the distal end of a medical device (e.g., distal end 214 of medical device 208) may be referred to herein as a fluid circuit.

Systems 200, 202 may further include a flow controller 216 within the fluid circuit between the fluid source 206, 206', respectively, and the distal end 214 of medical device 208. Flow controller 216 may include a valve, a solenoid, or other device configured to alter the flow of fluid within lumen 212. In some examples, flow controller 216 may be configured to apply negative pressure (or otherwise lower the positive pressure) to the fluid circuit to slow or stop the flow of fluid in a distal direction, or to reverse the flow of fluid within fluid circuit and cause the fluid to flow in a proximal direction. Flow controller 216 may be manually operated (e.g., via a switch pressed by a user) or may be integrated into the capital equipment (e.g., pump system) and controlled by electronics that are signaled by the user or otherwise programmed to control flow controller 216. When manually operated, the user may press a switch, a plunger, or other component to manually cause a valve or other device to transition from a first configuration to a second configuration to decrease fluid flow, lower the positive pressure, and/or apply negative pressure to the fluid circuit. When integrated into the capital equipment, either a trigger (e.g., positive pressure dropping below a certain threshold) or an action by the user (e.g., pressing a button or a switch) may relay a signal to electronics controlling the flow controller 216. The electrical signal may cause flow controller 216 to transition from a first configuration to a second configuration to alter the flow of fluid (e.g., by applying a negative pressure to the fluid circuit). In certain examples, at least a portion of flow controller 216 transitions from a first position to a second position when actuated by the electrical signal. Flow controller 216 may include a power supply. Furthermore, flow controllers 216 described herein, or features of the flow controllers 216, may be used in combination with one or more other flow controllers 216 described herein.

Referring to FIGS. 3A-3C, flow controller 216 may include a valve 316. The valve 316 may be integrated into the fluid circuit of systems 200, 202. FIG. 3A illustrates valve 316 in a first, injection position, FIG. 3B illustrates valve 316 in a second, suction position, and FIG. 3C illustrates valve 316 in a third, normal position. Valve 316 may include a first port 318, a second port 320, and a third port 322. Depending on the position of valve 316, first port 318 may be fluidly connected to fluid source 206, 206', second port 320 may be fluidly connected to lumen 212, and third port 322 may be fluidly connected to a suction source (not shown). Valve 316 may further include a first plug 324, a second plug 326, and a spring 328. First plug 324 may be fixed relative to second plug 326 by a shaft 330 to form an integrated unit. Accordingly, when one of first plug 324, shaft 330, or second plug 326 moves, the other attached components move as well.

Referring to FIG. 3A, in the injection position, the application of pressure from fluid flowing from fluid source 206, 206' may cause first plug 324 (and second plug 326) to move downwards (in the view of FIG. 3A) and depress spring 328. In this position, fluid from first port 318 may enter the body 332 of valve 316 and exit via second port 320. From second port 320, fluid may travel to distal end 214 of medical device 208 via lumen 212. In the position of FIG. 3A, first plug 324 may seal third port 322, which may connect to a suction source.

Referring to FIG. 3B, when pressurized fluid flow from fluid source 206, 206' is turned off or reduced, spring 328 may push against second plug 326, causing first plug 324 to block further fluid flow from first port 318 to second port 320. Without blocking further flow between first port 318 and second port 320, residual pressure can remain within the fluid circuit and cause fluid to continue to flow through lumen 212 and out of distal end 214 of medical device 208. When first plug 324 moves between first port 318 and second port 320, fluid communication may be opened between second port 320 and third port 322. Accordingly, the suction source connected to third port 322 may withdraw fluid from lumen 212, through second port 320, and through third port 322.

Referring to FIG. 3C, as positive pressure further reduces, spring 328 may continue to push second plug 326 upwards (in the view of FIG. 3C), until second plug 326 blocks second port 320 and third port 322. In this position, fluid is neither being injected through lumen 212 or withdrawn from lumen 212, and each of first, second, and third ports 318, 320, 322 may be fluidly disconnected from each other.

As illustrated in FIGS. 3A-3C, valve 316 operates to allow pressurized fluid from fluid source 206, 206' to flow through lumen 212 in a distal direction by opening fluid communication between first port 318 and second port 320 (FIG. 3A). However, upon a reduction of positive pressure from fluid source 206, 206', spring 328 may cause valve 316 to a) close fluid communication between first port 318 and second port 320, and b) open fluid communication between second port 320 and third port 322 (FIG. 3B). In the second position of FIG. 3B, a suction source may cause fluid to flow proximally through lumen 212. Finally, a further reduction or a cessation of positive pressure may allow valve 316 to transition to the third position of FIG. 3C, in which second plug 326 blocks fluid communications between each of first port 318, second port 320, and third port 322. In other examples, valve 316 may be operated (e.g., switched) using electronics and/or computer software, although the timing of the switches may coincide with the timing described in connection with the description related to switching facilitated by spring 328.

In an alternative example, valve 316 may be operated manually. Shaft 330 may be moved between the positions shown in FIGS. 3A-3C by depressing or pulling on actuator 301. When shaft 330 is in a desired position, the user may maintain the position of actuator 301 for a desired period of time.

Figure 4A:
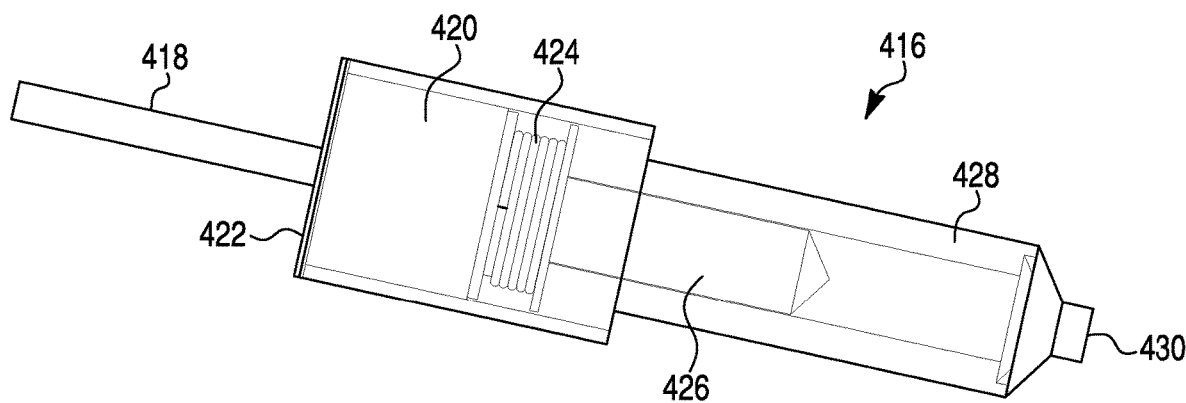
FIGS. 4A, 4B, and 4C illustrate a solenoid flow controller for applying negative pressure to a fluid lumen, according to an exemplary embodiment.
Figure 4B:
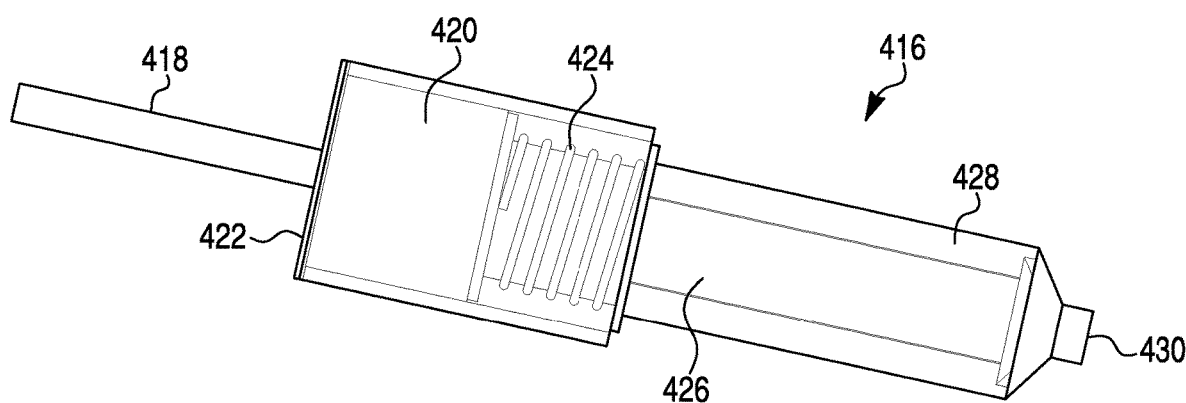
Figure 4C:
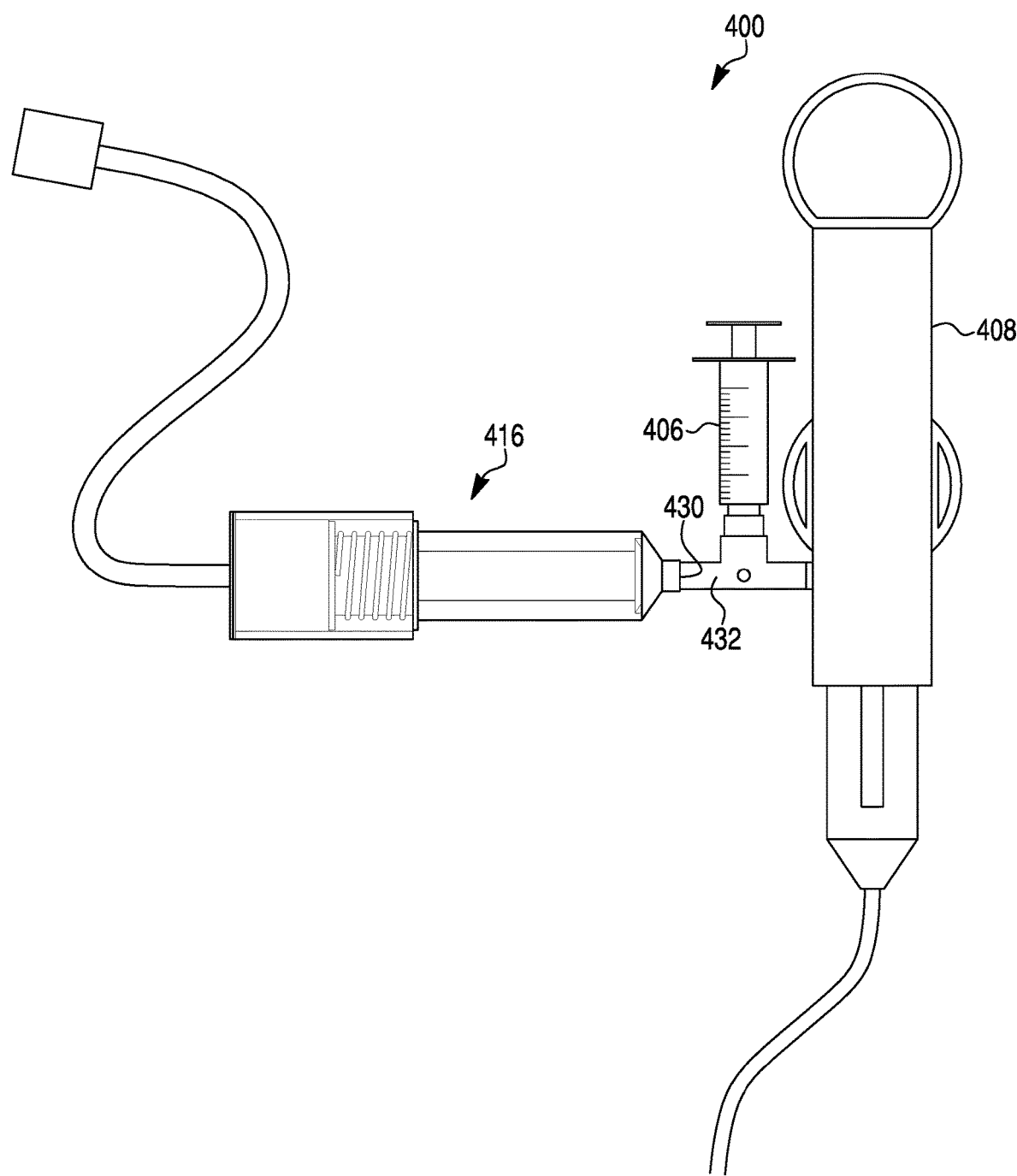

Referring to FIGS. 4A-4C, flow controller 216 may include a solenoid 416. Solenoid 416 may include a power supply 418, a solenoid coil 420, a coil stop 422, an extension spring 424, a plunger 426, and a syringe barrel 428. A distal end 430 of solenoid 416 may be fluidly connected to the fluid circuit between fluid source 206, 206' and distal end 214 of medical device 208. Solenoid 416 may transition from a first, on position shown in FIG. 4A to a second, off position shown in FIG. 4B. A switch (not shown) may control operation of solenoid 416. The switch may be manually controlled by a user or may be controlled by electronics and/or computer software to switch upon the occurrence of predefined conditions. When controlled by electronics and/or computer software, the solenoid 416 may be actuated to the "on" position when fluid source 206, 206' is turned off (e.g., stops supplying pressurized fluid to the fluid circuit) or when positive pressure through lumen 212 drops below a predefined threshold.

In the "on" position illustrated in FIG. 4A, current may be applied to the solenoid coil 420, magnetizing the armature of the solenoid (which is attached to plunger 426) and causing it to be attracted to coil stop 422. When the armature and plunger 426 actuate towards coil stop 422, a vacuum may be applied to the fluid circuit, preventing excess fluid from exiting distal end 214 of medical device 208. In some examples, the vacuum may cause fluid to flow proximally from the distal portion of lumen 212. To release the vacuum and allow positive pressure to be applied to the fluid circuit for injection, the current may be turned off (either manually or using electronics and/or computer software), allowing spring 424 to actuate plunger 426 to the second position shown in FIG. 4B.

FIG. 4C illustrates solenoid 416 integrated into a system 400. In addition to solenoid 416, system 400 may include a fluid source 406 (e.g., a syringe) and a medical device 408. Fluid source 406 and medical device 408 may include any of the features of fluid source 206 and medical device 208, respectively, described in connection with FIG. 2A. A three-way valve 432 may connect distal end 430 of solenoid 416, fluid source 406, and medical device 408. In one example, valve 432 is normally open, so that when solenoid 416 is on, a vacuum is applied to the fluid circuit between fluid source 406 and the distal end of medical device 408, and when solenoid 416 is turned off, the vacuum applied to the fluid circuit is released.

Figure 5A:
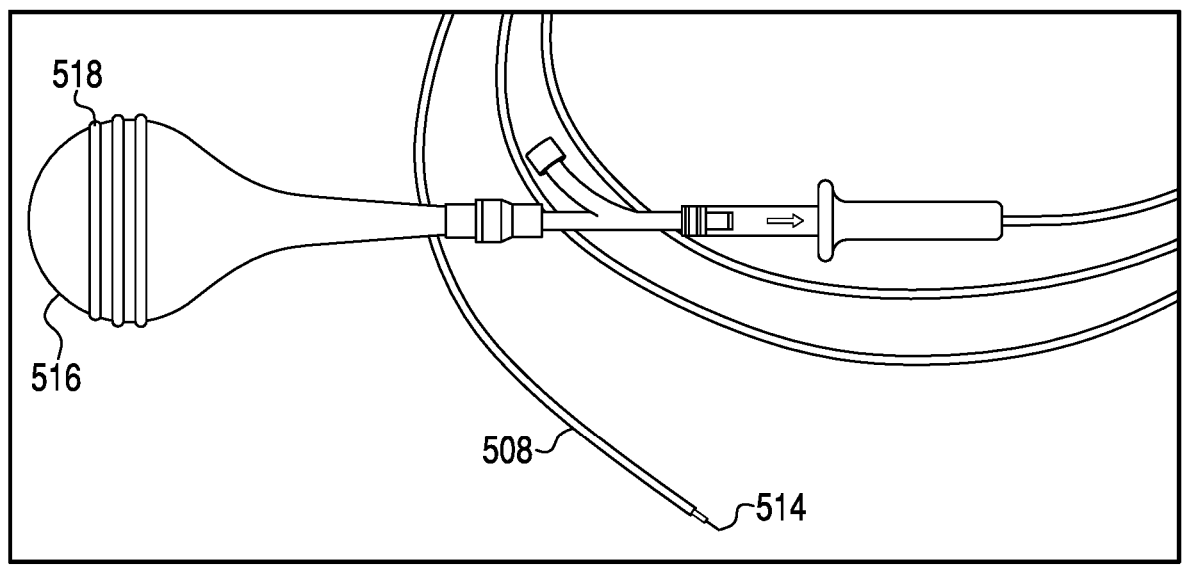
FIGS. 5A and 5B illustrate a bulb flow controller for applying negative pressure to a fluid lumen, according to exemplary embodiments.
Figure 5B:
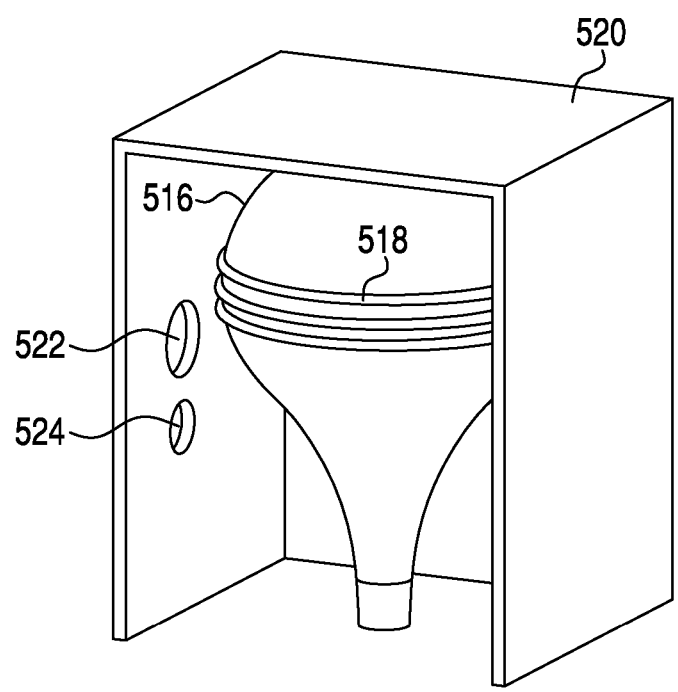

Referring to FIGS. 5A and 5B, flow controller 216 may include a container 516 having a feature 518 to bias the container 516 to an expanded position. FIG. 5 illustrates container 516 coupled to a medical device 508 having a distal end 514. Medical device 508 may include a lumen extending from a proximal end of medical device 508 to distal end 514, and may include any other features described in connection with medical device 208 of FIG. 2. Flow controller 516 may hold fluid and therefore may serve as a fluid source. Accordingly, flow controller 516 may be fluidly coupled to the lumen within medical device 508.

In the examples shown in FIGS. 5A and 5B, flow controller 516 can be collapsed and expanded by the application of external pressure. Feature 518 may include a ring or rings, webbing, wire formations, ribs, or any other feature that biases flow controller 516 to the expanded position. Flow controller 516 may include a substantially spherical portion, with an elongated spout protruding from the spherical portion, as shown in FIGS. 5A and 5B. In other embodiments, however, flow controller 516 may be a cube, a parallelepiped, an ovoid, or any other three-dimensional regular or irregular shape configured to hold fluid and to expand and contract to control fluid pressure.

In the expanded position shown in FIG. 5A, flow controller 516 may provide an ambient or negative pressure to any fluid in the fluid circuit between flow controller 516 and distal end 514 of medical device 508. In a collapsed position, flow controller 516 may apply a positive pressure to fluid within the fluid circuit. In FIG. 5A, the collapsed position may occur when a user squeezes or otherwise applies pressure to the outside of flow controller 516 to eject fluid out of distal end 514. When the user releases flow controller 516, a vacuum may be created within the fluid circuit, and fluid may be withdrawn from a distal portion of the lumen that extends through medical device 508. In other words, when external pressure is removed, flow controller 516 may return to the expanded configuration.

FIG. 5B illustrates an alternative configuration, in which external pressure may be applied to flow controller 516 by a pressure generator, instead of manually by a user. A pressure source (not shown) may be connected to an inlet 522 of a chamber 520. The chamber may further include an outlet 524. The pressure source may cause a fluid (e.g., liquid or compressed gas) to enter chamber 520, compressing flow controller 516 and ejecting fluid from distal end 514 of medical device 508 (see FIG. 5A). Once the application of positive pressure from pressure source is stopped, fluid in chamber 520 may exit via outlet 524, allowing flow controller 516 to return to its expanded configuration and apply a vacuum to the fluid circuit. In yet another example, the pressure source may apply a mechanical compression to flow controller 516. When the mechanical compression is released, flow controller 516 may return to its expanded configuration and apply a vacuum to the fluid circuit.

Figure 6A:
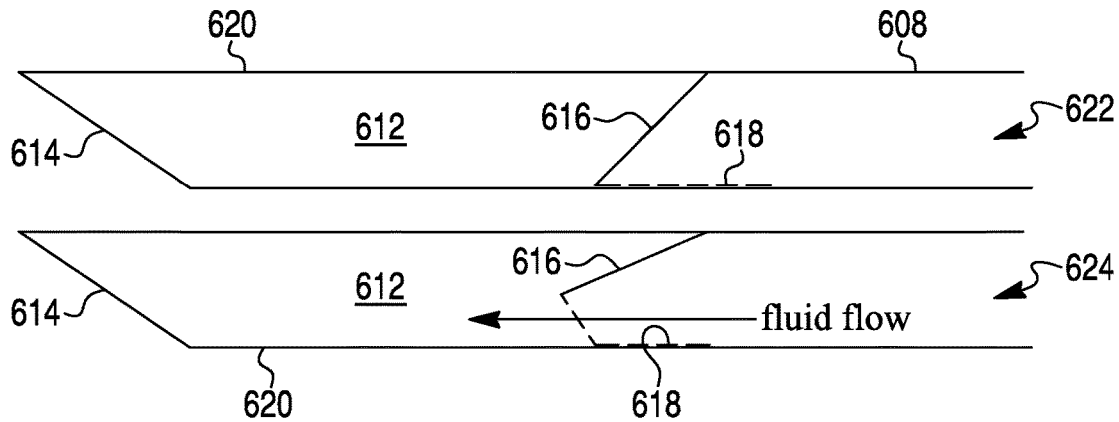
FIGS. 6A and 6B illustrate valve flow controllers for slowing or stopping fluid flow, according to exemplary embodiments.
Figure 6B:
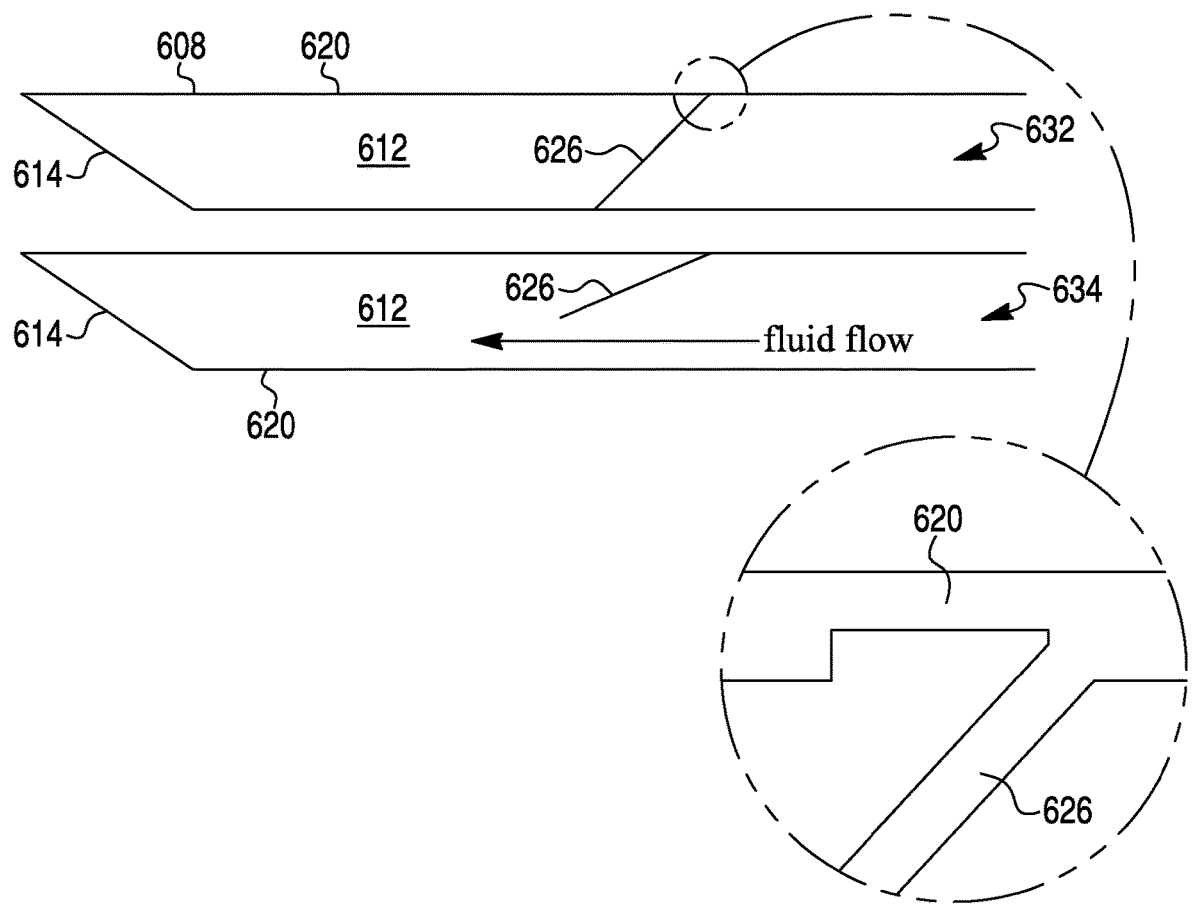

Referring to FIGS. 6A and 6B, flow controller 216 may include a valve 616, 626 that may be positioned proximate a distal end 614 of a medical device 608. The medical device 608 may include a needle. Referring to FIG. 6A, valve 616 may be coupled to a permeable layer 618. Permeable layer 618 may be rigid or flexible and may lie against and parallel to an inner surface of a wall 620 that defines a lumen 612 of medical device 608. Permeable layer 618 may help anchor valve 616 in a first, closed configuration 622. Accordingly, valve 616 may be biased to remain in the closed configuration 622, in which valve 616 may block fluid from flowing in a distal direction and out of distal end 614. In a second, open configuration 624, valve 616 may allow distal flow of fluid out of distal end 614.

When positive pressure introduces fluid into lumen 612 of medical device 608, the positive pressure may cause valve 616 to transition from closed configuration 622 to open configuration 624. When transitioning to open configuration 624, valve 616 may pull permeable layer 618 into the path of fluid flow. The pressure of the fluid may be sufficient to pass through permeable layer 618. However, when the pressure source (not shown) is turned off, pressure within lumen 612 proximal to valve 616 may decrease, and fluid may no longer be sufficiently pressurized to pass through permeable layer 618. Furthermore, the reduction in pressure may allow permeable layer 618 to return to its position against wall 620, pulling valve 616 back to the closed configuration 622.

The permeability of permeable layer 618 and the pressure required to move valve 616 from the closed configuration 624 to the open configuration 622 may be selected such that fluid flow from distal end 614 is stopped when pressure proximal to valve 616 drops below a certain threshold. For example, flow from distal end 614 may stop immediately or very shortly after the pressure source is turned off, even if residual pressure remains proximal to valve 616. In addition, the valve 616 may be used in combination with any other flow controllers described herein.

FIG. 6B illustrates valve 626. In one example, valve 626 may be cut from the material of wall 620, as shown in the exploded view. In other examples, valve 626 may be soldered or otherwise fixed to an interior of wall 620. Similar to valve 616, valve 626 may be biased to a closed configuration 632 and may transition to an open configuration 634 by the application of fluid pressure. The pressure required to transition valve 626 from closed configuration 632 to open configuration 634 may be selected such that valve 626 stops the flow of fluid immediately or shortly after the pressure source is turned off, even if residual pressure remains in lumen 612 proximal to valve 626.

Figure 7A:
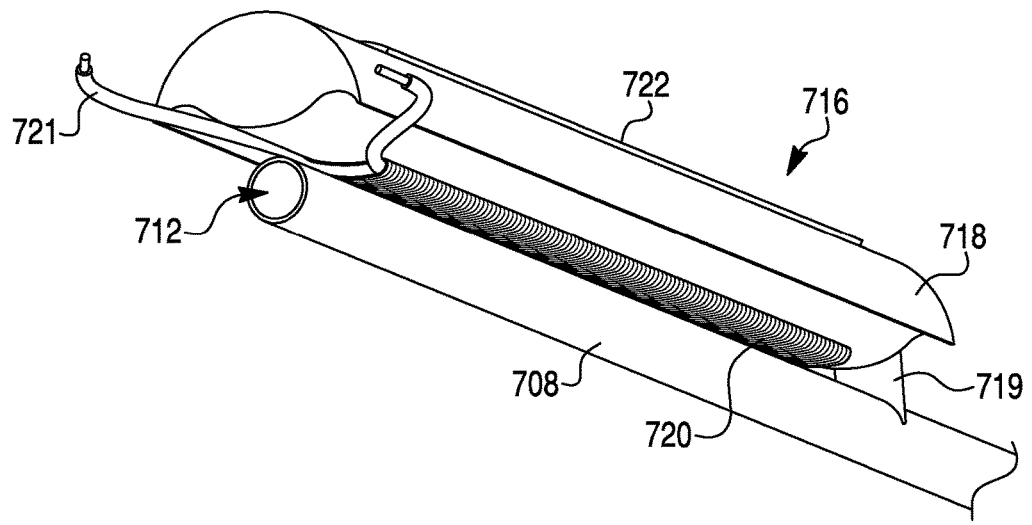
FIGS. 7A and 7B illustrate an electromagnetic flow controller for applying negative pressure to a fluid lumen, according to an exemplary embodiment.
Figure 7B:
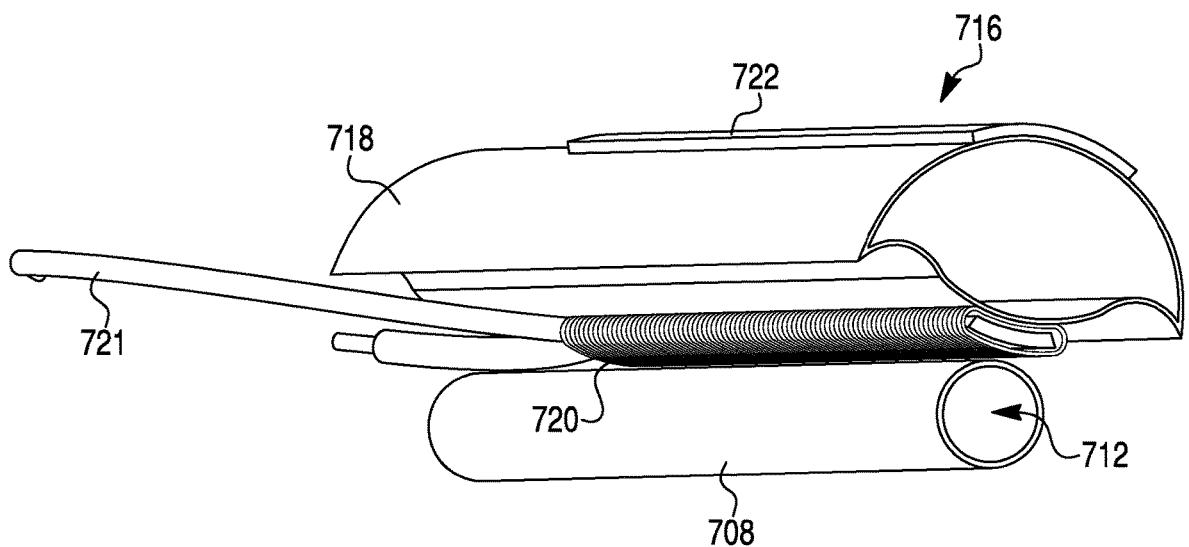

FIGS. 7A and 7B illustrate flow controller 716 that may include a bladder 718 (e.g., a container), an electromagnet 720, and a magnet 722. Bladder 718 may be fluidly connected to a lumen 712 of a medical device 708 via a port 719. Bladder 718 may contain fluid, and therefore may serve as a fluid source. Electromagnet 720 may include a core and a wire wrapped around the core, with one or more wires 721 carrying current to the electromagnet. Electromagnet 720 and magnet 722 may be positioned on opposite sides of bladder 718. Furthermore, bladder 718 may be biased to a first, expanded configuration, as shown in FIGS. 7A and 7B. Medical device 708 may include any of the features described in connection with medical device 208 of FIG. 2.

When a user desires to apply positive pressure to fluid within lumen 712, the user may turn on a current to magnetize electromagnet 720. Electromagnet 720 and magnet 722 may then pull towards each other, squeezing bladder 718 into a second, collapsed configuration to eject fluid from bladder 818 and cause positive pressure to be applied to fluid within lumen 712. Fluid may then be pushed out of a distal end (not shown) of medical device 708. When the user stops the application of positive pressure by turning the current off (either manually or using electronics and/or computer software), electromagnet 720 may be demagnetized (or lowered in magnetic strength), and bladder 718 may self-expand back to the first, expanded configuration. The expansion of bladder 718 may cause negative pressure to be applied to fluid within lumen 712, and may stop and/or slow the flow of fluid in a distal direction and/or cause fluid to flow proximally, away from the distal end of medical device 708.

FIGS. 8A-8D illustrate a flow controller 816 that may include a fluid source 806, a reservoir 818, a switch 820, and a secondary pressure source 822, in addition to other components to be described below. Fluid source 806 (e.g., a syringe) may be actuated by a primary pressure source, such as a user (as shown in FIG. 8A-8D) or a mechanism controlled by electronics and/or computer software. Fluid source 806 may be fluidly coupled to lumen 812 of medical device 808. Reservoir 818 also may be fluidly coupled to lumen 812 of medical device 808. Reservoir 818 may include a spring 824 coupled to a plunger 826. Secondary pressure source 822 may be a tank of compressed air that at times is fluidly connected, via switch 820, to a lumen 828 leading to reservoir 818.

Figure 8A:
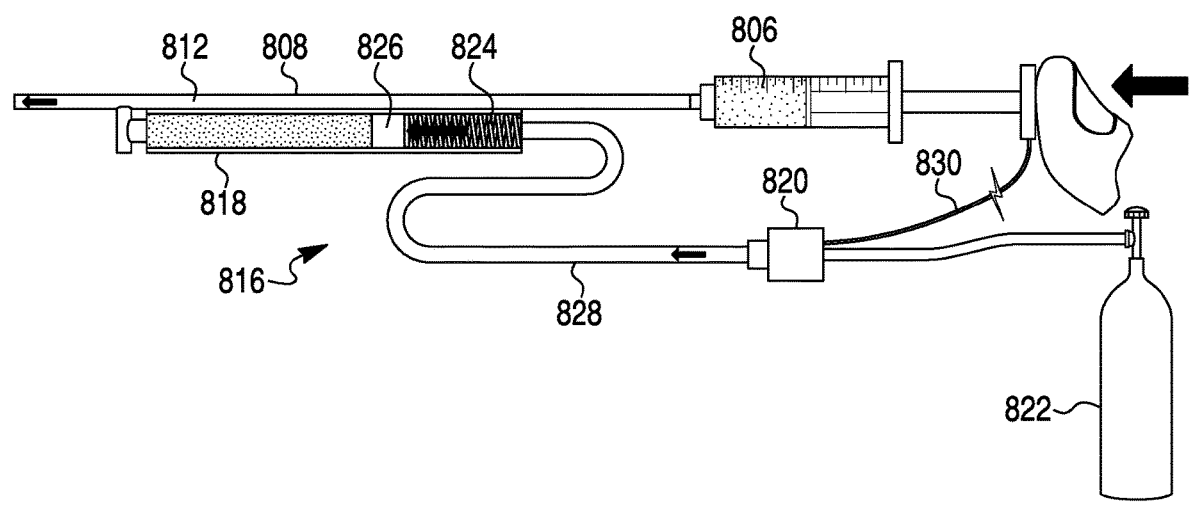
FIGS. 8A, 8B, 8C, and 8D illustrate a system using a reservoir flow controller to apply negative pressure to a fluid lumen, according to an exemplary embodiment.
Figure 8B:
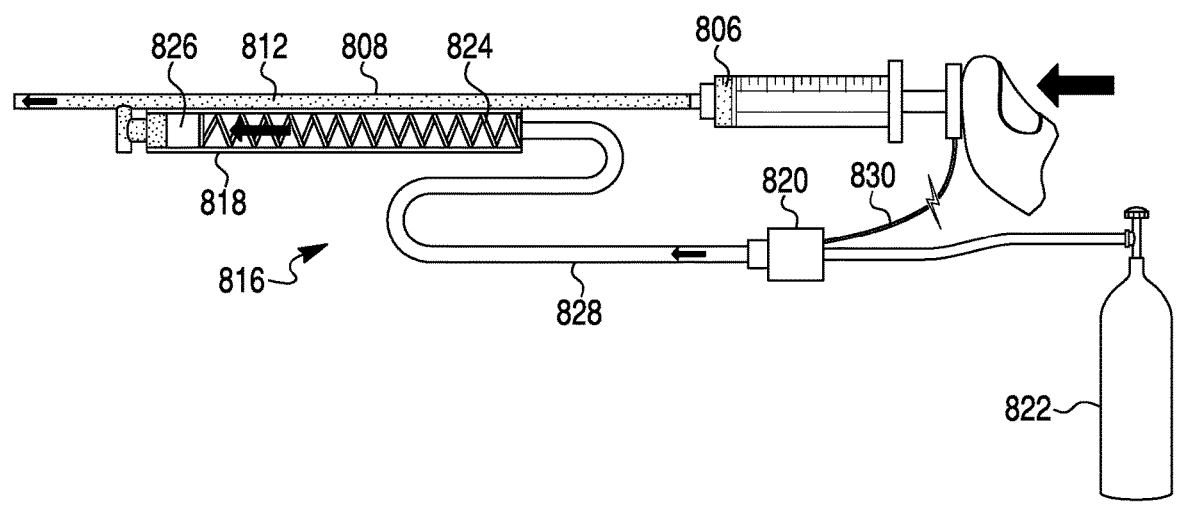

During operation of medical device 808 to inject fluid, fluid source 806 may be actuated to cause fluid to flow from fluid source 806 through lumen 812. At the same time, an electrical communication may be sent via one or more wires 830 to switch 820, causing switch 820 to open. As shown in FIGS. 8A and 8B, when switch 820 opens, compressed air may flow from secondary pressure source 822, through lumen 828, and to reservoir 818. The compressed air may push down plunger 826, which in turn extends spring 824. Plunger 826 may cause fluid within reservoir 818 to flow into lumen 812 of medical device 808.

Figure 8C:
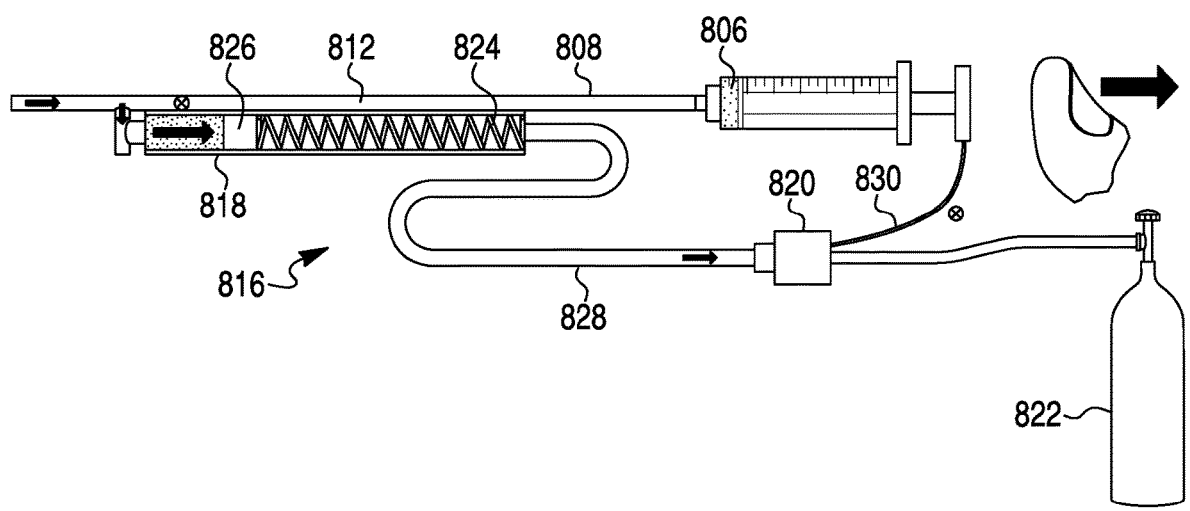
Figure 8D:
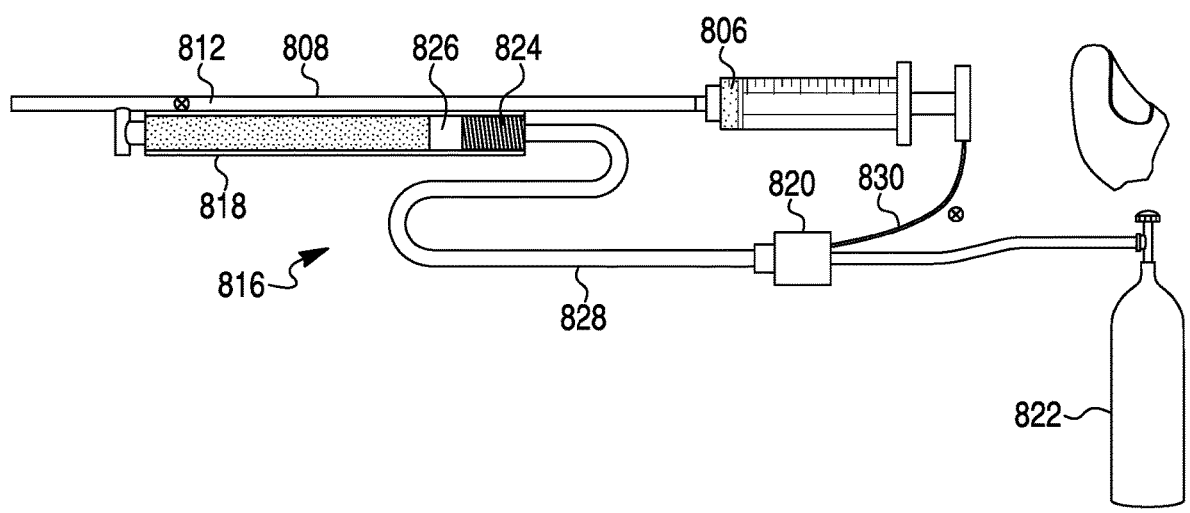

When the user releases pressure on fluid source 806, as shown in FIG. 8C, another electrical signal may cause switch 820 to close. The closing of switch 820 may cut off the flow of compressed air from secondary pressure source 822 to reservoir 818. The force of spring 824 returning to a compressed configuration may pull plunger 826 back towards a proximal end of reservoir 818, creating a vacuum force and pulling fluid from lumen 812 back into reservoir 818 (see FIGS. 8C and 8D). Accordingly, when the application of positive pressure from fluid source 806 is stopped or lowered, the system shown in FIGS. 8A-8D operates to create a negative pressure within the fluid circuit. Reservoir 818 may supply fluid to lumen 812 during a flow of fluid from fluid source 806, and withdraw fluid from the lumen after a user has either removed a positive pressure source (e.g., removed his/her finger) or otherwise signaled fluid source 806 to discontinue the flow of fluid (e.g., via electronics and/or computer software). The negative pressure created by reservoir 818 may slow or stop the flow of fluid from the distal end of medical device 809, or may cause fluid to flow proximally through lumen 812.

Figure 9A:
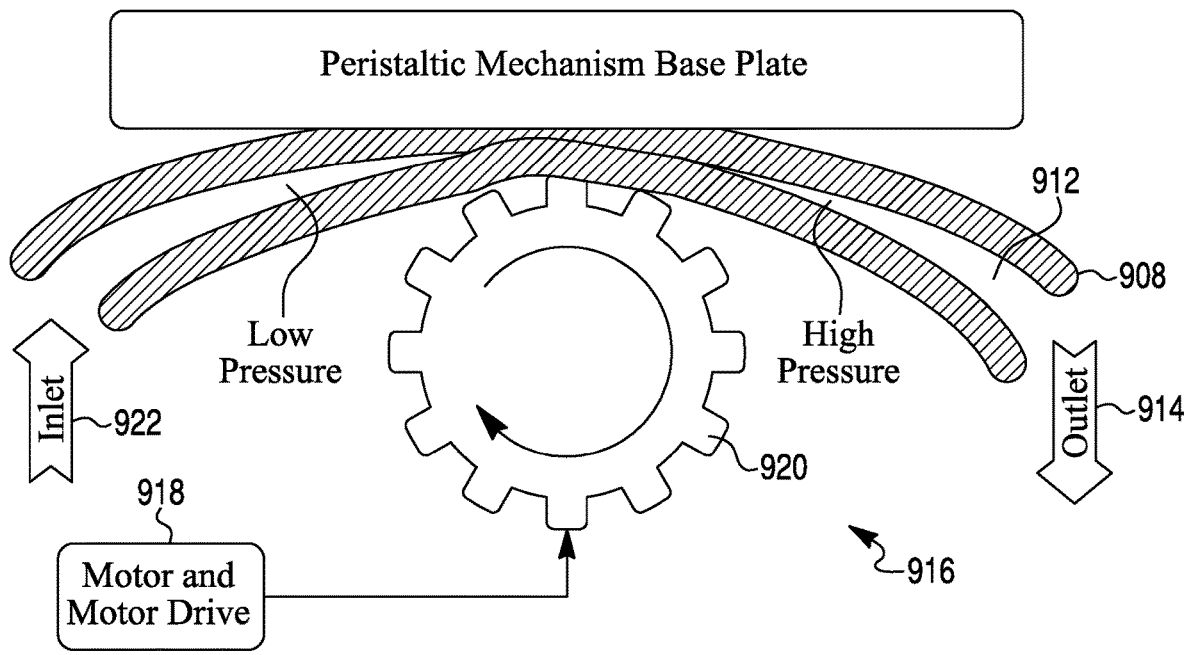
FIGS. 9A and 9B illustrate the use of a peristaltic mechanism for applying negative pressure to a fluid lumen, according to an exemplary embodiment.
Figure 9B:
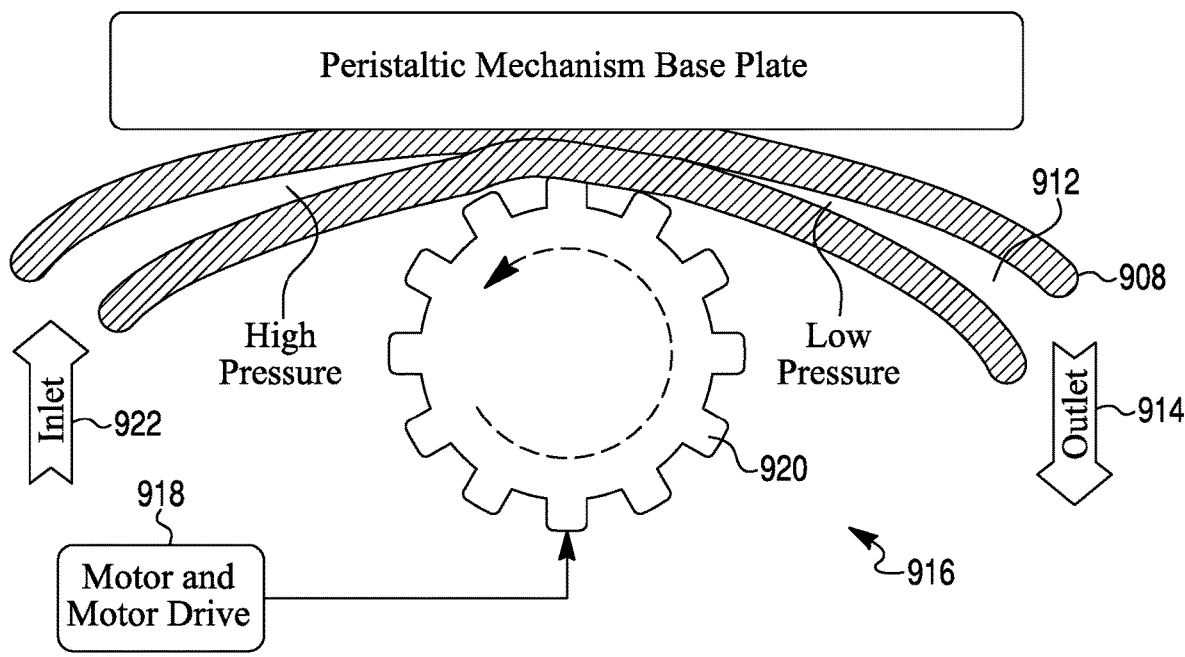

Referring to FIGS. 9A and 9B, flow controller 216 may include a peristaltic pump 916. Peristaltic pump 916 may include a motor 918 having a gear 920. Gear 920 may contact fluid lumen 912, shown in cross-section in FIGS. 9A and 9B. Fluid lumen 912 may be part of a medical device 908. Accordingly, fluid lumen 912 may be part of a fluid circuit that extends from an inlet 922 (e.g., coupling a fluid source to lumen 912) to an outlet 914 (e.g., a distal end of a medical device).

When gear 920 of peristaltic pump 916 rotates in the direction shown in FIG. 9A, fluid downstream from gear 920 may be pressurized and pushed towards outlet 914. In addition, fluid upstream of gear 920, towards inlet 922, may decrease in pressure, pulling fluid from the fluid source (not shown). When a user stops fluid delivery (e.g., at the end of an injection procedure), motor 918 may be configured to cause gear 920 to rotate in an opposite direction, as shown in FIG. 9B, for a predetermined period of time. The reverse rotation may lower the fluid pressure downstream of gear 920, which may slow or stop flow of fluid in a distal direction and/or cause fluid to flow in a proximal direction, away from outlet 914.

While principles of the present disclosure are described herein with reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

We claim:

1. A method for performing a medical procedure, comprising:
   introducing a distal end of a medical device to a region proximate a target tissue, including inserting the distal end into a submucosal layer of tissue;
   applying a positive pressure to a fluid within a single lumen of the medical device to cause fluid from a fluid source to exit the distal end to lift the target tissue;
   lowering an application of the positive pressure, wherein lowering the application of the positive pressure below a threshold triggers a mechanical switch or an electrical signal in a flow controller to apply negative pressure from a negative pressure source to the fluid within the single lumen such that the fluid within the single lumen flows in a proximal direction; and
   cutting the target tissue;
   wherein the flow controller includes:
      a fluid container fluidly connected to the single lumen of the medical device;
      an electromagnet; and
      a magnet, wherein the magnet and the electromagnet are each positioned on opposite external sides of the fluid container, and wherein the magnet and the electromagnet are configured to move toward one another in order to apply the positive pressure to the fluid.

2. The method of claim 1, wherein the medical device includes an electrosurgical cutting tool at the distal end of the medical device, and cutting the target tissue includes cutting the target tissue using the electrosurgical cutting tool.

3. The method of claim 1, wherein lowering of the application of the positive pressure causes (A) the mechanical switch to cause the flow controller to apply the negative pressure to the fluid within the single lumen, or (B) the electrical signal to be sent to the flow controller to cause the flow controller to apply the negative pressure to the fluid within the single lumen.

4. The method of claim 3, wherein the mechanical switch or the electrical signal causes at least a portion of the flow controller to move from a first position to a second position.

5. The method of claim 1, wherein the electromagnet is magnetized during the application of the positive pressure, and lowering the application of the positive pressure includes lowering a magnetic strength of the electromagnet.

6. A method for performing a medical procedure, comprising:
   introducing a distal end of a medical device to a region proximate a target tissue;
   applying a positive pressure to a fluid within a single lumen of the medical device to cause the fluid to exit the distal end of the medical device and enter a space underneath or within the target tissue to lift the target tissue,
      wherein an application of the positive pressure moves a plunger contained within a valve to a first configuration, wherein the plunger includes a first plug, a second plug, and a shaft extending between the first plug and the second plug, wherein, in the first configuration, the first plug is positioned to permit fluid communication between a first port of the valve and a second port of the valve and prevent fluid communication between both of the first and second ports and a third port of the valve, wherein, in the first configuration, the second port is between the first port and the first plug, and
      wherein the shaft of the plunger defines a longitudinal axis, wherein the first port and the second port are positioned on a first side of the longitudinal axis, and wherein the third port is positioned on a second side of the longitudinal axis, opposite the first side; and
   lowering the application of the positive pressure below a threshold, wherein lowering the application of the positive pressure below the threshold triggers a mechanical switch or an electrical signal of a flow controller to move the plunger contained within the valve to a second configuration, wherein, in the second configuration, the first plug is between the first port of the valve and the second port of the valve so as to prevent fluid communication between the first port of the valve and the second port of the valve, and the second port of the valve and the third port of the valve are between the first plug and the second plug to permit fluid communication between the second port of the valve and the third port of the valve so as to apply a negative pressure to the fluid within the single lumen such that fluid within the single lumen flows in a proximal direction.

7. The method of claim 6, wherein lowering of the application of positive pressure causes (A) the mechanical switch to cause the flow controller to apply the negative pressure to the fluid within the single lumen, or (B) the electrical signal to be sent to the flow controller to cause the flow controller to apply the negative pressure to the fluid within the single lumen.

8. The method of claim 6, wherein the first port of the valve is configured to be fluidly connected to a fluid source, the second port of the valve is configured to be fluidly connected to the single lumen of the medical device, and the third port of the valve is configured to be fluidly connected to a negative pressure source.

9. A system for controlling a flow of fluid through a medical device, comprising:
   a medical device having a single lumen that extends to a distal end of the medical device, wherein the medical device includes an electrosurgical cutting tool;
   a fluid source configured to supply fluid having a positive pressure to the single lumen of the medical device, wherein the medical device is configured to eject fluid from the distal end of the medical device while supplying fluid having a positive pressure from the fluid source to lift a target tissue; and
   a flow controller having a valve with a valve body, wherein the valve includes a plunger contained within the valve body, wherein the plunger includes a first plug, a second plug, and a shaft extending between the first plug and the second plug, and wherein the valve body defines a first port configured to be fluidly connected to the fluid source, a second port configured to be fluidly connected to the single lumen of the medical device, and a third port configured to be fluidly connected to a negative pressure source;
   wherein, to apply a positive pressure to the fluid within the single lumen to cause the fluid to flow in a distal direction within the single lumen, the flow controller is configured such that the plunger is in a first configuration, wherein, in the first configuration, the second port is between the first port and the first plug so as to permit fluid communication between the first port and the second port and prevent fluid communication between both of the first and second ports and the third port,
   wherein to apply a negative pressure from the negative pressure source to the fluid within the single lumen to cause the fluid to flow in a proximal direction within the single lumen, the flow controller is configured such that the plunger is in a second configuration, wherein, in the second configuration, the first plug of the plunger permits fluid communication between the second port and the third port,
   wherein, upon a lowering of the positive pressure from the fluid source below a threshold, the flow controller is triggered via a mechanical switch or an electrical signal to move the plunger from the first configuration to the second configuration to apply the negative pressure,
   wherein, upon a further lowering of the positive pressure from the fluid source, the flow controller moves the plunger from the second configuration to a third configuration, wherein, in the third configuration, the second plug prevents fluid communication between the first port, the second port, and the third port such that the flow of fluid from the distal end of the medical device is slowed or stopped.

10. The system of claim 9, wherein the lowering of the positive pressure is configured to cause (A) the mechanical switch to cause the flow controller to apply the negative pressure to the fluid within the single lumen, or (B) the electrical signal to be sent to the flow controller to cause the flow controller to apply the negative pressure to the fluid within the single lumen.

11. The method of claim 6, further comprising cutting the target tissue using the medical device, wherein the medical device includes an electrosurgical cutting tool at the distal end of the medical device, and cutting the target tissue includes cutting the target tissue using the electrosurgical cutting tool.

12. The method of claim 1, wherein the medical device includes a visualization system, wherein the visualization system includes a light source and a system to transmit image signals.

13. The method of claim 6, wherein further lowering the application of the positive pressure moves the plunger to a third configuration, and wherein, in the third configuration, the first port of the valve is between the first plug and the second plug, and the second plug prevents fluid communication between the first port of the valve, the second port of the valve, and the third port of the valve.

14. The system of claim 9, wherein, in the second configuration, the third port is between the second port and the second plug.

15. The system of claim 9, wherein, in the third configuration, the first port is between the first plug and the second plug.

16. The system of claim 9, wherein the flow controller includes a spring, wherein the spring is positioned between the second plug and a valve body of the valve, and wherein, during an application of positive pressure, the spring is depressed, and during lowering the application of the positive pressure, the spring is raised.

17. The method of claim 6, wherein, in the second configuration, the third port is between the second port and the second plug.

18. The system of claim 9, wherein the shaft of the plunger defines a longitudinal axis, wherein the first port and the second port are positioned on a first side of the longitudinal axis, and wherein the third port is positioned on a second side of the longitudinal axis, opposite the first side.

19. The method of claim 13, wherein, in the third configuration, the second plug intersects the second port of the valve and the third port of the valve, such that the second plug blocks the second port of the valve and the third port of the valve.

20. The system of claim 9, wherein, in the third configuration, the second plug intersects the second port of the valve and the third port of the valve, such that the second plug blocks the second port of the valve and the third port of the valve.

* * * * *